US007148706B2

(12) United States Patent
Srinivasan et al.

(10) Patent No.: US 7,148,706 B2
(45) Date of Patent: Dec. 12, 2006

(54) EMBEDDABLE CORROSION RATE METERS FOR REMOTE MONITORING OF STRUCTURES SUSCEPTIBLE TO CORROSION

(75) Inventors: Rengaswamy Srinivasan, Ellicott City, MD (US); Hassan M. Saffarian, Silver Spring, MD (US); Terry E. Phillips, Ellicott City, MD (US)

(73) Assignee: Johns Hopkins University, Baltimore, MD (US)

( * ) Notice: Subject to any disclaimer, the term of this patent is extended or adjusted under 35 U.S.C. 154(b) by 142 days.

(21) Appl. No.: 10/517,364

(22) PCT Filed: Jul. 18, 2003

(86) PCT No.: PCT/US03/22606

§ 371 (c)(1),
(2), (4) Date: Dec. 8, 2004

(87) PCT Pub. No.: WO2004/010104

PCT Pub. Date: Jan. 29, 2004

(65) Prior Publication Data

US 2006/0125480 A1   Jun. 15, 2006

Related U.S. Application Data

(60) Provisional application No. 60/409,330, filed on Sep. 9, 2002, provisional application No. 60/396,694, filed on Jul. 18, 2002.

(51) Int. Cl.
*G01R 27/08* (2006.01)
(52) U.S. Cl. ...................... 324/700; 324/693
(58) Field of Classification Search ............ 324/700, 324/693
See application file for complete search history.

(56) References Cited

U.S. PATENT DOCUMENTS 3,601,693 A   8/1971   Lorentzen (Continued)

FOREIGN PATENT DOCUMENTS

DE         35 11706        10/1986

(Continued)

*Primary Examiner*—Andrew H. Hirshfeld
*Assistant Examiner*—Amy He
(74) *Attorney, Agent, or Firm*—Albert J. Fasulo, II

(57) ABSTRACT

An embeddable corrosion rate meter (ECRM) for detecting and measuring corrosion in metal and concrete structures is provided. The system comprises an electrochemical cell with at least one working electrode evenly separated from a counter electrode, wherein a separation distance between electrodes determines an electrolyte medium resistance and the electrolyte medium resistance is less than or equal to a polarization resistance. The system further includes a signal generator connected to a plurality of resistances for creating a plurality of current amplitudes for generating a current source; a first selector for applying a current through each of the plurality of resistances to the working electrode and counter electrode; a second selector for selecting a duration of a current pulse; a voltmeter/A-D converter having an input impedance $>10^9$ ohms for measuring polarization of the working electrode; and an external reader-head with a data link and power link connected to a computing device for powering the system and collecting corrosion measurements data.

13 Claims, 8 Drawing Sheets

U.S. PATENT DOCUMENTS

| | | | |
|---|---|---|---|
| 3,788,962 A | 1/1974 | Franck | |
| 3,939,408 A | 2/1976 | Brown | |
| 4,155,814 A * | 5/1979 | Tejfalussy et al. | 205/776 |
| 4,238,298 A | 12/1980 | Tsuru et al. | |
| 4,275,352 A | 6/1981 | Sudar et al. | |
| 4,339,719 A | 7/1982 | Rhines et al. | |
| 4,513,248 A | 4/1985 | Miller | |
| 4,571,466 A | 2/1986 | Iida | |
| 4,682,113 A | 7/1987 | Barben, II | |
| 4,751,466 A | 6/1988 | Colvin et al. | |
| 4,780,664 A | 10/1988 | Ansuini et al. | |
| 4,793,175 A | 12/1988 | Fedter et al. | |
| 4,800,165 A | 1/1989 | Oka et al. | |
| 4,808,931 A | 2/1989 | Ling | |
| 4,863,572 A | 9/1989 | Jasinski | |
| 4,958,130 A | 9/1990 | Mochizuki et al. | |
| 5,179,347 A | 1/1993 | Hawkins | |
| 5,403,550 A | 4/1995 | Wietek | |
| 5,448,178 A | 9/1995 | Chen et al. | |
| 5,519,330 A | 5/1996 | Yamauchi et al. | |
| 5,674,375 A | 10/1997 | Thompson | |
| 5,712,559 A | 1/1998 | Moore et al. | |
| 5,792,337 A | 8/1998 | Padovani et al. | |
| 5,854,557 A | 12/1998 | Tiefnig | |
| 5,855,721 A | 1/1999 | Monteiro et al. | |
| 5,895,843 A | 4/1999 | Taylor et al. | |
| 6,012,337 A | 1/2000 | Hodge | |
| 6,057,693 A | 5/2000 | Murphy et al. | |
| 6,132,593 A | 10/2000 | Tan | |
| 6,223,129 B1 | 4/2001 | Chan et al. | |
| 6,320,395 B1 | 11/2001 | Bosch et al. | |
| 6,690,182 B1 * | 2/2004 | Kelly et al. | 324/700 |
| 2002/0057097 A1 | 5/2002 | Kelly et al. | |
| 2003/0011387 A1 | 1/2003 | Trejo et al. | |

FOREIGN PATENT DOCUMENTS

| | | |
|---|---|---|
| DE | 35 17772 | 11/1986 |
| WO | WO 88/09498 | 12/1988 |
| WO | WO 99/58990 | 11/1999 |
| WO | WO 02/46701 | 6/2002 |
| WO | WO 03/006958 | 1/2003 |

* cited by examiner

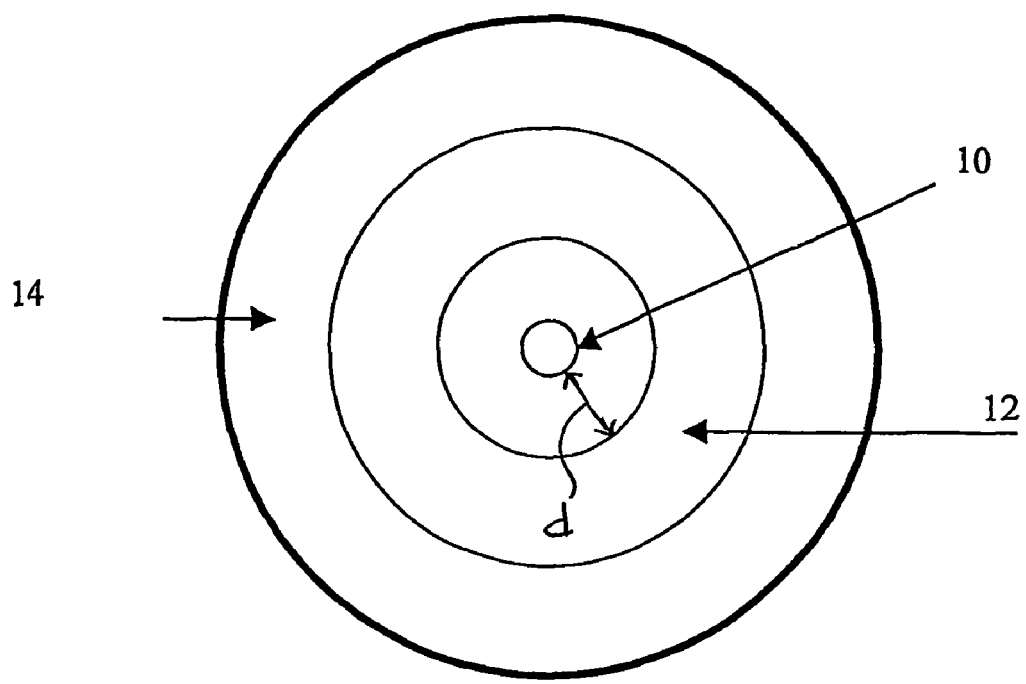
Figure 1A A Ring-Disc Sensor Assembly (not drawn to scale)
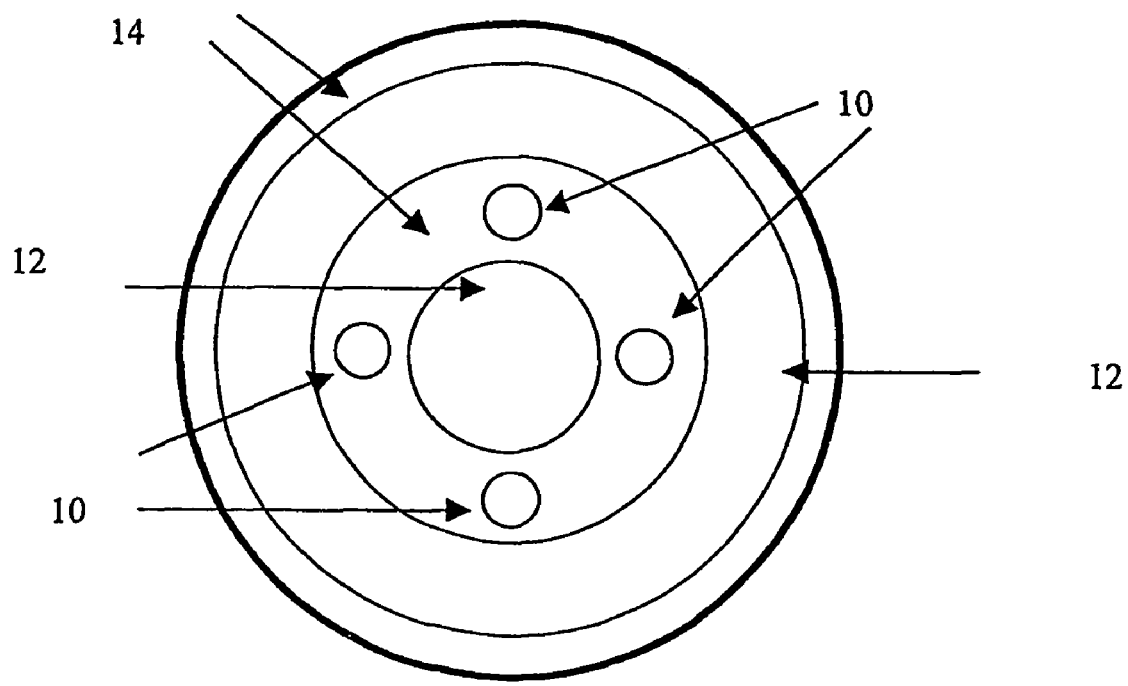
Figure 1B A Multiple Sensor Assembly (not drawn to scale)

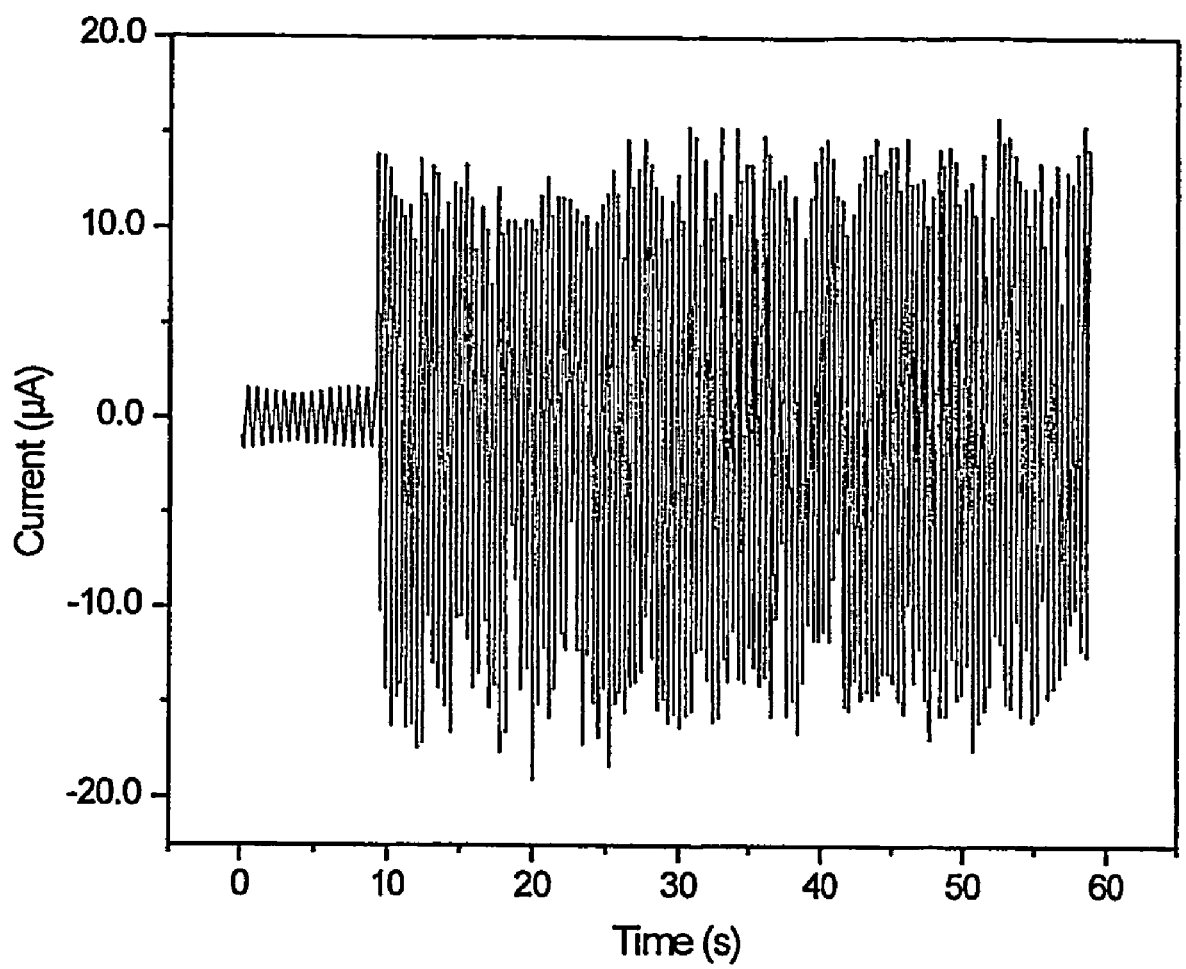
Figure 5. Current pulse output from the Galvanostat.

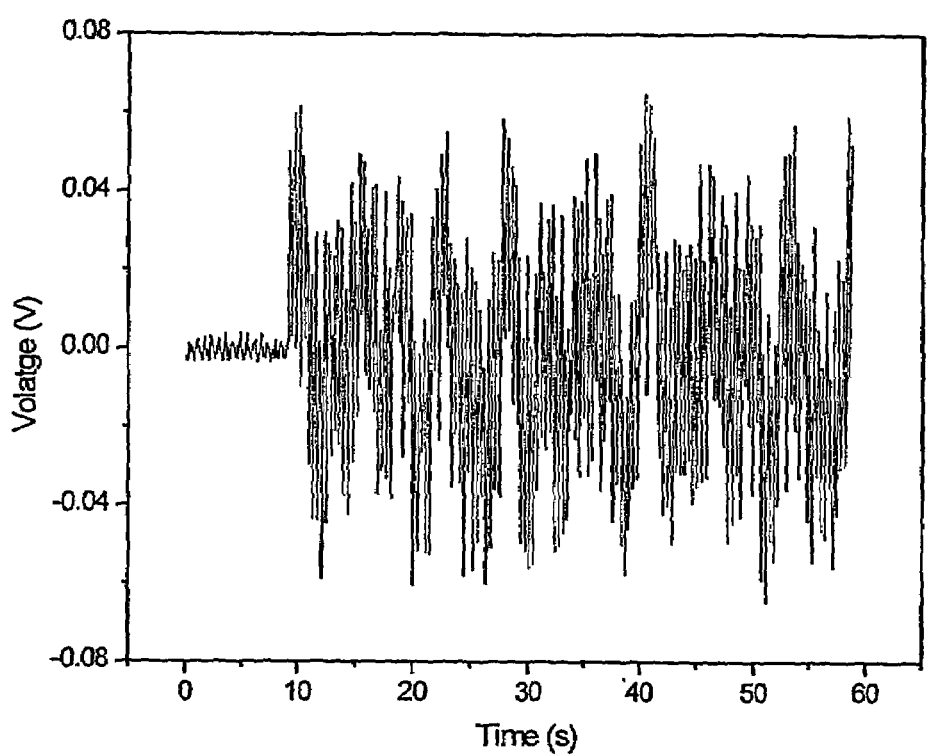
Figure 6. Voltage response by the Electrochemical Cell to the current input shown in Figure 5.

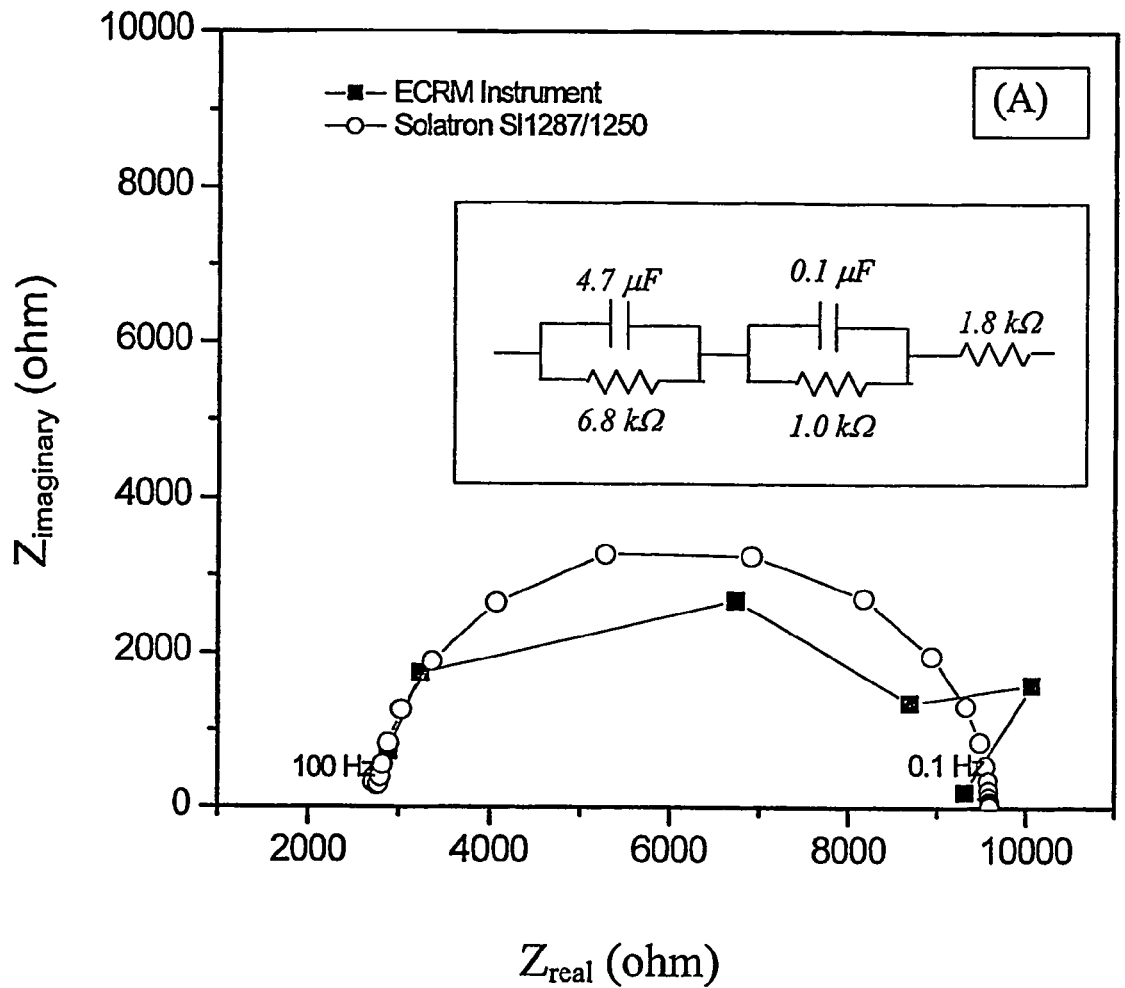

Figure 7a. Impedance of the Dummy Cell Solartron ECI Test Module 12861. The inset shows the electrical components in Module 12861. Note that the two instruments have measured and identified 6,800 ohms as the difference in the $Z_{real}$ values between 0.1 Hz and 100 Hz. Similarly, the $Z_{real}$ value at 100 Hz is 2,800 ohm, which is the sum of 1,000 ohm and 1,800 ohm. In a real corrosion cell, the $Z_{real}$ value at the high-frequency limit (100 Hz) would represent the electrolyte resistance (or the concrete resistance $R_{conc}$), and the difference in the $Z_{real}$ values between the low- and high-frequency limits (0.1 Hz and 100 Hz) would represent the $R_p$.

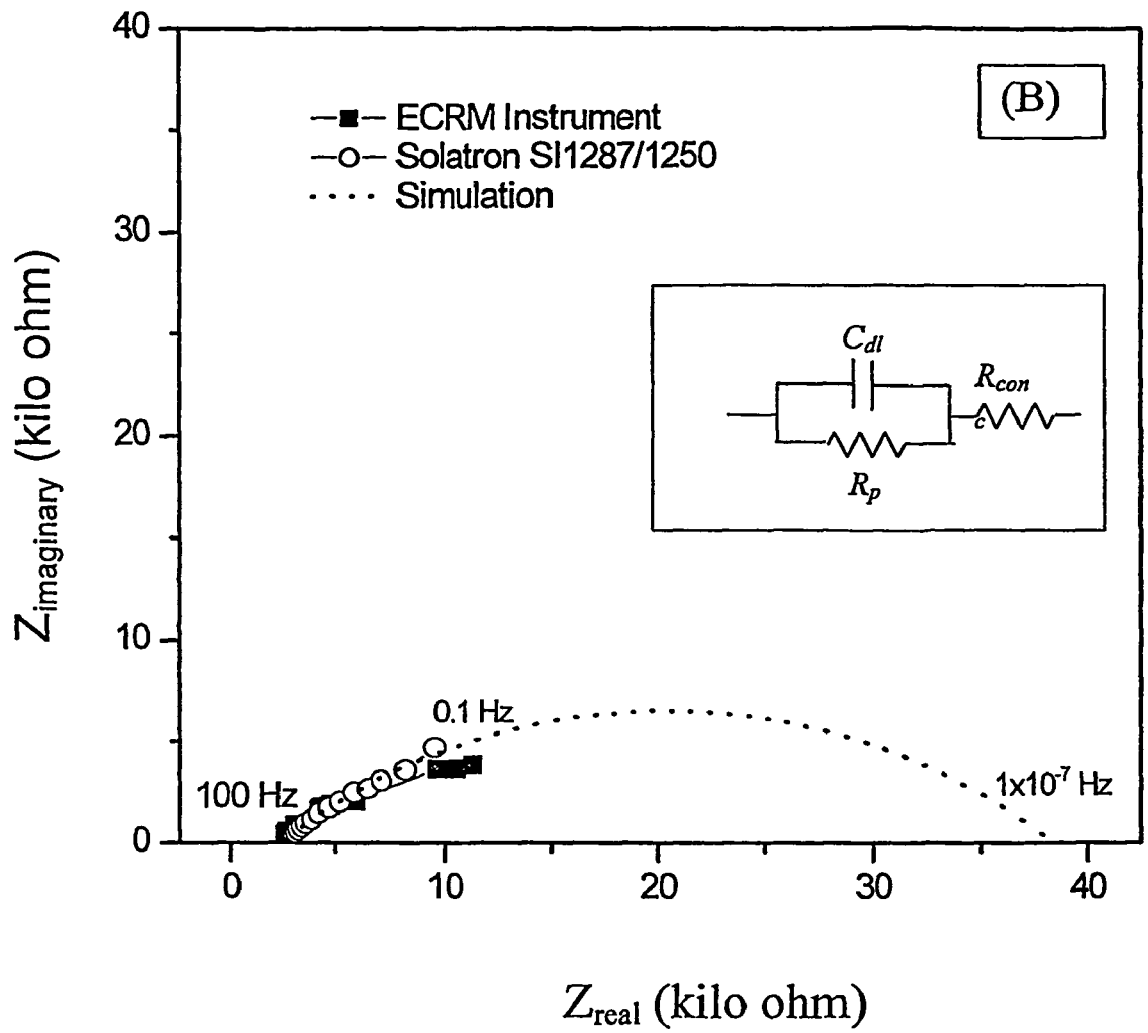
Impedance measured by the Solartron SI 1287/1250 (- o -).
Impedance measured by the inventive instrument (- ■ -).
Figure 7B. Impedance of the Electrochemical Cell with steel embedded in concrete.

EMBEDDABLE CORROSION RATE METERS FOR REMOTE MONITORING OF STRUCTURES SUSCEPTIBLE TO CORROSION

CROSS-REFERENCE TO RELATED APPLICATION

This application is a national stage of international application no. PCT/US03/22606, filed Jul. 18, 2003, and claims priority to U.S. Provisional Application Nos. 60/396,694, filed on Jul. 18, 2002, and 60/409,330, filed on Sep. 9, 2002, the contents of which are incorporated by reference herein.

BACKGROUND OF THE INVENTION

1. Field of the Invention

The present invention relates generally to Embeddable Corrosion Rate Meter (ECRM) instrumentation for remote monitoring of structures susceptible to corrosion.

2. Description of the Related Art

The basic operating principles of the Embeddable Corrosion Rate Meter (ECRM) instrumentation works on the principles of a technique known as chronovoltammetry, i.e., Voltage-Time Response. However, recent changes to the instrumentation part of the ECRM provides the flexibility of using principles of yet another technique, known as alternating current (AC) impedance or Electrochemical Impedance Spectroscopy (EIS), to estimate corrosion rates. The ECRM instrumentation or sensor contains a test electrode that is perturbed or excited with one or more current (I) pulses. The time-dependent changes (response) in the electrochemical potential (Y) of the electrode are measured.

Alternatively, a set of constant potential pulses can be used as the perturbation signal to measure the resulting current transients (chronoamperommetry) and estimate the corrosion rates. This notwithstanding, the rest of the application is directed to chronovoltammetry. The ECRM instruments or sensors are small, comparable in size to concrete aggregates and require very little electric power to operate. The electronic circuit necessary for making the instrument is relatively simple. The use of chronovoltammetry allows ECRM instruments to work in electrolytes, such as concrete, that are not good conductors of electricity.

The (V/I) ratio, also known as the polarization resistance, $R_p$, is inversely proportional to the corrosion rate. The conventional corrosion rate measurement techniques such as linear polarization and logarithmic polarization also estimate $R_p$ described in "Testing of Concrete in Structures", Ed. J. H. Bungey and S. G. Millard, Blackie Academic & Professional, NY, Third Edition, 1996, p. 173. These techniques use a direct current (DC) or voltage source to perturb the electrode and measure the DC voltage or current response using relatively simple electronic circuitry. However, the conventional corrosion rate measurement techniques are not useful in measuring corrosion rates when the metal is in contact with mediums that are poor conductors of electricity. These techniques suffer from an error caused by the resistive drop, also known as "IR-Drop", that occurs when the current passes through the resistive medium. Therefore, the use of linear and logarithmic polarization techniques could result in erroneous estimation of corrosion rates.

There are also techniques based on alternating current (AC) principles. For example, AC impedance or electrochemical impedance spectroscopy (EIS) can measure $R_p$ more accurately than the DC techniques, but it requires complex electronic circuits. The chronovoltammetry-based ECRM employs a relatively simple electronic circuit, overcomes the problem of IR-Drop, can be designed to be small, and requires very little power to operate. ECRM, which is an ideal corrosion rate meter, is embeddable in concrete or soil to measure corrosion rates of steel reinforcing bars (rebars), pipelines, and other buried structures.

Similar to linear and logarithmic polarization, and EIS techniques, the ECRM also uses principles of electrochemistry to measure corrosion rates. In essence, all electrochemical techniques apply a known voltage to the metal under test, and measure the resulting current flow across the metal/electrolyte (concrete) interface. Alternatively, in some cases, the perturbing signal is a known current, and the resulting change in the voltage across the metal/electrolyte interface is measured; the resistance across the electrode/electrolyte interface is the polarization resistance, $R_p$. The current-voltage relationship provides the rate of corrosion of the metal in the medium (concrete).

A major problem with most techniques is the electrical resistance of the concrete: the current that flows through the concrete generates a voltage drop, $V_{conc}=IR_{conc}$ (IR-Drop) across its resistance. Thus, the voltage applied or measured is V, which is the sum of $IR_{conc}$ and $IR_p$; $IR_{conc}=V_{conc}$; $IR_p=V_p$; and $V=V_{conc}+V_p$. In concrete, $R_{conc}$ can be much larger than $R_p$, and unless the correction is made for the voltage drop, $V_{conc}$, across $R_{conc}$, the corrosion rate will be grossly underestimated. Most electrochemical techniques suffer from this limitation, and some of them use chronovoltammetry for the IR-Drop correction. In other words, they combine chronovoltammetry for IR-Drop correction with yet another technique to measure the rate of corrosion. An obvious, practical limitation is using at least two types of electronics and instrumentation, one for IR-Drop correction, and another for corrosion rate measurement.

SUMMARY OF THE INVENTION

The inventive technique uses chronovoltammetry for both $R_{conc}$ estimation and for corrosion rate estimation. Thus, the electronic circuit used is the same, which is a particular advantage while designing miniature, embeddable instruments. The instrument used to implement the technique is about the size of a small pebble, normally found as aggregates in concrete, and is compatible with the device known as the Smart Aggregate. The technique to implement corrosion rate measurements in, for example, concrete, using ECRM is described below.

Accordingly, in one embodiment of the present invention, an embeddable system for detecting and measuring corrosion in a structure susceptible to corrosion is provided, said system including a plurality of embeddable corrosion rate meters ECRM) for collecting corrosion measurements data and at least one computing device for analyzing said corrosion measurements, said system comprising:

at least one working electrode evenly separated from a counter electrode, wherein a separation distance between said at least one working electrode and said counter electrode determines an electrolyte medium resistance, said electrolyte medium resistance is less than or equal to a polarization resistance;

a signal generator for generating a current source, said current source is connected to a plurality of resistances for creating a plurality of current amplitudes;

a first selector for applying current through each of said plurality of resistances to said at least one working electrode and said counter electrode, wherein said current is applied via a galvanostat; and, an external reader-head with a data link and power link connected to said computing device for powering said ECRM and transferring corrosion measurements data via said data link.

A second embodiment of the present invention is a method for detecting and measuring corrosion in a structure susceptible to corrosion, said corrosion being detected by a plurality of embeddable corrosion rate meters (ECRM) and analyzed by at least one computing device, said method comprising the steps of:

determining an electrolyte medium resistance using a separation distance between at least one working electrode and said counter electrode, said at least one working electrode evenly separated from a counter electrode, wherein a electrolyte medium resistance being less than or equal to a polarization resistance;

generating a current source connected to a plurality of resistances for creating a plurality of current amplitudes;

applying a current from a first selector through each of said plurality of resistances to said at least one working electrode and said counter electrode, wherein said current is applied via a galvanostat;

selecting via a second selector, a duration of a current pulse; measuring polarization of said working electrode using a voltmeter/A-D converter, wherein said voltmeter has an input impedance greater than $10^9$ ohms; and, powering said system via a power link connected to an external reader-head and collecting corrosion measurements data via a data link connected to said external reader-head, wherein said external reader-head is connected to said computing device.

BRIEF DESCRIPTION OF THE DRAWINGS

The above and other objects, features and advantages of the present invention will become more apparent from the following detailed description when taken in conjunction with the accompanying drawings in which:

FIG. 1A is a diagram illustrating a ring-disc sensor assembly including a working electrode and a counter/reference electrode of the present invention;

FIG. 1B is a diagram illustrating a multiple sensor assembly including four working electrodes and two counter/reference electrode of the present invention;

FIG. 5 is a graph of current I over time showing the current pulse output from the galvanostat of the present invention;

FIG. 6 is a graph of voltage V over time showing the voltage response of the electrochemical cell to the current input from the galvanostat of the present invention, shown in FIG. 5;

FIG. 7A is a graph of impedance of the Dummy Cell Solartron ECI Test Module 12861, with an equivalent $R_p$ of 6,800 ohms; and, FIG. 7B is a graph of impedance of the Electrochemical Cell with steel embedded in concrete.

DETAILED DESCRIPTION OF THE PREFERRED EMBODIMENTS

Figure 2:
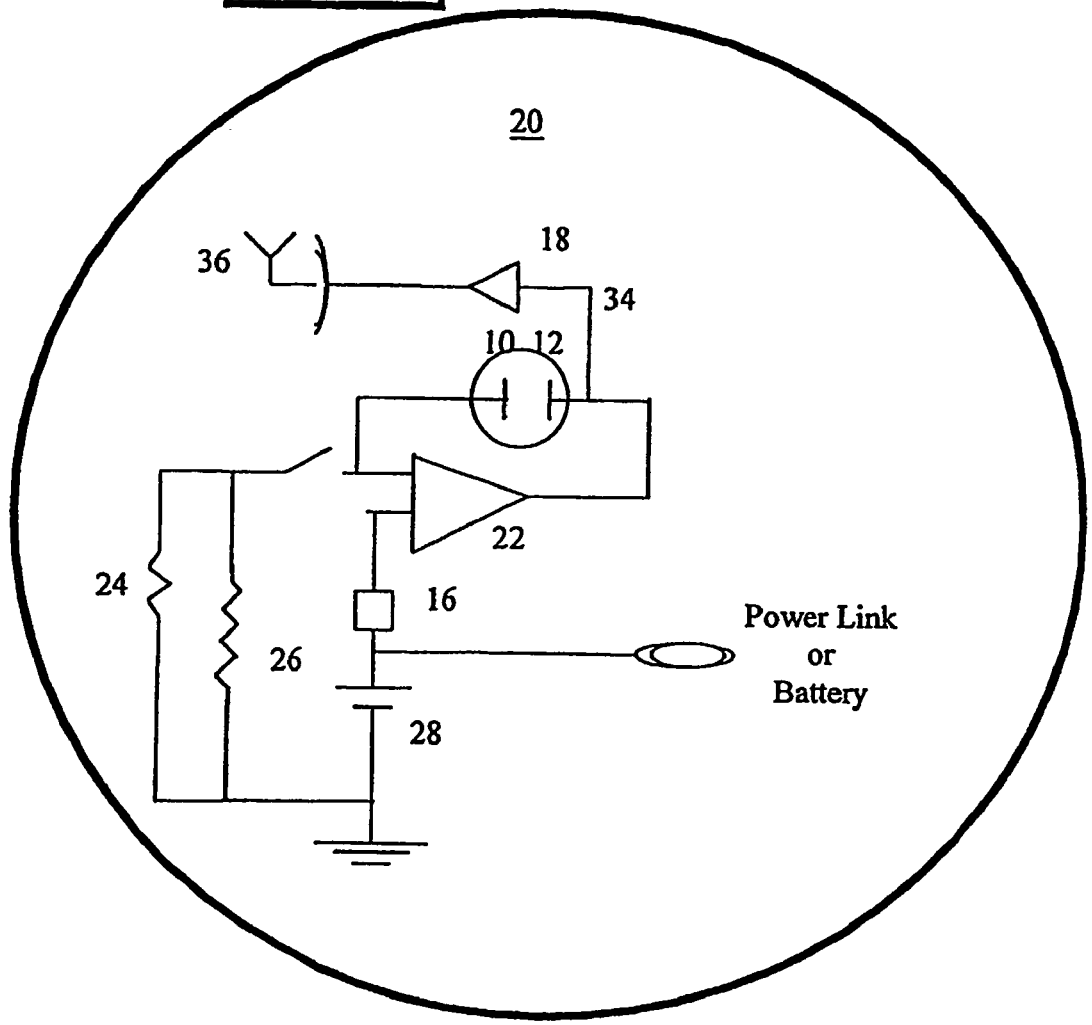
FIG. 2 is an electrical diagram representing an Embeddable Corrosion Rate Meter (ECRM) sensor circuit of the first embodiment.

First, it should be pointed out that a rebar in concrete is always corroding. The rate of corrosion is generally so small that it has no adverse effect on concrete. However, in addition to water, low pH and oxygen, when a corrosive agent such as chloride or salt gets to the surface of the rebar, then the rate of corrosion will increase thereby resulting in damage to the structure. The inventive Embeddable Corrosion Rate Meter (ECRM) technology described herein measures the corrosion rate directly, instead of inferring it from the concentrations of various chemicals, i.e., corrosive agents, which initiate and sustain corrosion.

The ECRM identifies the transition of the rate from being small and below the threshold to above the threshold of causing corrosion damage. It is important to identify the transition, since if the measurement indicates a rebar is already corroding above the critical limit, it could be too late to prevent potential damage to concrete. The issue of early identification of the onset of the above-threshold corrosion rate is addressed herein by measuring the corrosion rates of a section of rebar material placed vertically above the reinforcing rebar. When corrosive agents penetrate into concrete, they do so by starting from the surface of the concrete and moving inward. A rebar material corrosion rate sensor placed in the path of the corrosive agents at one or more locations before the agents reach the reinforcing bars will serve the purpose of forewarning the impending corrosion to the rebars.

Advantages of Direct Measurement of Corrosion Rate

Before describing the design of the corrosion rate sensor, ECRM is first compared with a Conductivity Sensor in Smart Aggregate (SA), which also senses changes in the corrosive environment of concrete. The SA is fully described in U.S. patent application Ser. No. 10/220,102, filed on Aug. 27, 2002. The Conductivity Sensor is described in the U.S. patent application Ser. No. 10/344,000, filed on Feb. 6, 2003.

The intended purpose of the corrosion sensor is identical to the pH, $CO_2$, or conductivity sensor: to identify the incoming corrosive agents, e.g., acid rain, $CO_2$, and chloride, and indirectly determine when corrosion will initiate in the rebars. The corrosion rate sensor has an important advantage over the other sensors, namely, it more directly measures the corrosion rate. The rest of the sensors only measure parameters that are potentially related to corrosion, and may need input about a number of variables for accurate data interpretation. A conductivity sensor used in monitoring chloride concentration, for example, is an "indirect" sensor; relating conductivity data to chloride concentration depends upon a number other variables, including moisture content, temperature and the amount of chloride bound to the silicates in concrete. On the other hand, the corrosion meter provides corrosion rate data at any temperature, moisture, or chemical properties of the electrolyte medium like concrete. Moreover, a conductivity sensor will report an increase in the conductivity, if sodium chloride is co-present with sodium sulfate. The later is present in brackish water and seawater, and unlike rainwater mixed with chloride, does not attack a steel rebar aggressively. A conductivity sensor cannot tell the difference in conductivity caused by a benign salt dissolved in brackish water over an aggressive salt dissolved in rainwater.

Furthermore, dry salt, without moisture, does not alter the electrical conductivity in concrete. Concrete, in general, is highly non-conducting, and inclusion of salt should increase the conductivity of concrete. Laboratory measurements on concrete samples mixed with various amounts of sodium chloride, i.e., common salt, have shown that the conductivity does vary by more than one order of magnitude when the concentration of the salt in concrete is increased to about 3,500 ppm, as described on page 170 of the above referenced "Testing of Concrete in Structures". Recent measurements conducted at The Johns Hopkins University Applied Physics Laboratory have raised some questions in correlating corrosion rate with conductivity. There is, of course, no question that salt does increases conductivity in concrete. However, it also appears that water in wet concrete also increases the conductivity. While salt alone or water alone increase conductivity in concrete, there is no way of telling the degree of contribution from salt and water without a priori knowledge of the concentration of either the salt or the water. That means, that a salt sensor, that specifically measures the concentration of chloride, and water and humidity sensor, to identify the level of water, are necessary to determine the individual contributions of salt and water to the overall measured conductivity. Even if these two sensors were used, they do not necessarily measure the total amount of salt or water present in the concrete, which depends upon how the chloride ions and water molecules are bound to the other chemical components in cement, therefore, may or may not contribute to the measured conductivity.

Chloride tends to bind to the silicates, and water to calcium hydroxide, both major components of concrete, and the degree of binding may depend upon the age of concrete. Once bound, those ions and molecules contribute toward conductivity to a lesser degree, and the degree of contribution from each is differently dependent upon temperature. Thus, predicting corrosion information from conductivity data could become intractable, unless pH, wetness, and temperature data are known. The conductivity sensor may still be a useful indicator of potential presence of salt inside concrete, but its usefulness depends upon developing an accurate physicochemical model of conductivity vs. chemical/physical properties of concrete.

Corrosion rate data, unlike conductivity data, tell us if the corrosion rate has increased or not. Parameters that accentuate corrosion of steel in concrete are well documented in the literature, for example (a) Proceedings of the symposium on *Corrosion of Reinforcement in Concrete*, 21–24 May 1990, Ed. C. L. Page, K. W. Treadaway and P. B. Bamforth, Published for Society for Chemical Industry by Elsevier Applied Science, NY, pp. 281–384;

(b) Properties of Concrete, Ed. A. M. Neville, John Wiley & Sons Inc., NY, 1996;

(c) *Life Prediction of Corrodible Structures*, Ed. R. N. Parkins, NACE International, Houston, Tex. 1994, Section 4 Concrete, p. 52; and, (d) C. E. Locke, "Corrosion of Steel in Portland Cement Concrete: Fundamental Studies," in *Corrosion Effect of Stray Current and the Techniques for Evaluating Corrosion of Rebars in Concrete*, ASTM Special Technical Publication 906, Ed. V. Chaker, ASTM, PA, 1984, p. 5.

Salt is just one of the agents that cause corrosion in a steel rebar. Water alone does not increase the rate of corrosion, it is the dissolved oxygen in water that does. The rate of corrosion for a fixed amount of salt is dependent on the pH of concrete. Concrete, typically has a pH in the range of about 13 to about 13.5 and at that pH steel rebars do not corrode. Moreover, as long as the pH of concrete is within the range of about 13 to about 13.5, it does not corrode even in the presence of small amount of chloride, e.g., about 350 ppm, an amount commonly found in deiced surfaces of concrete bridge decks. The dependence of the corrosion rate on the pH of the electrolyte (concrete) containing various amounts of chloride is described in the literature, for example, (e) Lectures on Electrochemical Corrosion, Ed. M. Porbaix, Plenum Press, NY, 1973, p. 271; and, (f) Properties of Concrete, Ed. A. M. Neville, John Wiley & Sons Inc., NY, 1996, p. 566.

However, if the pH decreases from about 13 to about 12, then the rate of corrosion will be substantially higher in the presence of about 350 ppm chloride as compared to an absence of chloride, see references (e) and (f) above. If the pH decreases to about 11, the rate of corrosion caused by the same amount of chloride increases by several orders of magnitude as compared to the rate at pH about 13. Acid rain, domestic sewage, and atmospheric $CO_2$ can and do decrease the pH of concrete from about 13.5 to substantially lower values where the concrete is prone to corrosion, see page 560 of "Properties of Concrete, Ed. A. M. Neville, John Wiley & Sons Inc., NY, 1996". The corrosion rate data obtained using the ECRM sensor do not require conductivity, pH, moisture, oxygen concentration, or chloride content data for interpreting the results. The corrosion rate is useful as such, without compensation for the chemical and physical composition of concrete. Thus, the ECRM is superior to conductivity, humidity, oxygen, or pH sensors. ECRM also provides answers to the only question that all other sensors are attempting to infer: how long will it take before the steel reinforcing bars begin to corrode at rates that are significant and detrimental to the structure?

The Corrosion Rate Sensor

FIGS. 1A and 1B illustrate two suggested corrosion rate sensor designs, a single and multiple sensor assembles; and it should be recognized that other variations of the sensor designs are possible. In both designs, there is at least one working electrode (WE) 10 and one counter/reference electrode (CRE) 12. The WE 10 is made from the same material as the subject that is undergoing corrosion; in the case of concrete, the WE 10 is made from the same steel alloy as the rebar used in reinforcing the concrete. The CRE 12 is made from a non-corroding, inert material such as, for example, nickel, mixed-metal oxide, e.g., titanium oxide+ruthenium oxide, graphite or 'dimensionally stable' palladium-coated titanium. If necessary, although less desirable, the same material as the WE 10, i.e., steel, can be used as the CRE 12. It is quite important to keep the area of the WE 10 small; CRE 12 should be at least 25× larger than WE 10. In all the designs, the separation distance between the perimeter edges of the WE 10 and the CRE 12 can be 0.1 cm or more, limited only by the distance allowed by the inner diameter of the external CRE 12, and the diameter of the central CRE 12 (FIG. 1*b*).

For example, in FIG. 1A WE 10 is about 0.3 cm in diameter and CRE 12 is about 2.0 cm in outside diameter (OD) and about 1.3 cm in inside diameter (ID), and in FIG. 1B each WE 10 is about 0.2 cm in diameter, the external CRE 12 region is about 2.0 cm OD and about 1.6 cm ID and the central CRE 12 region is about 0.8 cm in diameter. In the design shown in FIG. 1B, each WE 10 is interrogated separately for corrosion rate. The ratio between the surface areas of the WE 10 and CRE 12 should be at least about 1:25, the CRE 12 being about 25-times larger than the WE 10. If it turns out that the rebar material should be used for the CRE 12, then the area of WE 10 and CRE 12 could be equal, and the sum of the areas of the two electrodes should be accounted for when estimating the corrosion rate. In other designs, the CRE 12 can have a cylindrical projection of several millimeters above the top surface of the sensor; in these designs, the cylindrical surface will add to the total area of the CRE 12.

The separation distance (d) between the edges of the WE and the CRE determines the electrolyte medium, e.g., concrete, resistance, $R_{conc}$. The resistance associated with the corrosion rate, $R_p$, also known as the polarization resistance, is independent of d. Since the primary objective of the corrosion rate sensor is to measure $R_p$, it is important to keep the $R_{conc} \leq R_p$; it also provides critical advantage from instrumentation perspective of keeping most of the dynamic range of the measurement devices to measure $R_p$ rather than $R_{conc}$. The sensor designs described in FIG. 1A take the $R_{conc}$ vs. $R_p$ relationship into account, and provide the maximum advantage to make accurate measurements of $R_p$.

A ring-disc design of the corrosion sensor is described in FIG. 1A. The suggested shape for the WE 10 is a disc with a surface area of about 0.071 cm$^2$ or about 0.3 cm in diameter. The CRE is a ring with a flat surface; the OD and the ID are about 2.0 and about 1.3 cm, respectively. The surface area of the CRE 12 is about 1.8 cm$^2$. The WE 10 and CRE 12 are positioned concentrically; it allows a uniform current density distribution over the two electrodes during rate measurements. The disc shaped WE 10 and the ring shaped CRE are laid on an inert support, exposing only the flat top surfaces. The exposed front surfaces of the WE and CRE are in contact with the medium, i.e., concrete. The two electrodes are connected from their masked backside to the input terminals of the Corrosion Rate Meter, which will be described below with reference to FIG. 2 and FIG. 4.

FIG. 1B illustrates an alternate WE/CRE design for the sensor. It allows for measuring of the distribution of corrosion rate over the area of the sensor. It consists of a CRE 12 split into a ring and a disc. The ring has an OD and an ID of about 2.0 and about 1.6 cm, respectively; and the disc is about 0.8 cm in diameter. The ring and the disc are electrically connected to each other and together form the CRE 12. The total surface area of the CRE is about 1.63 cm$^2$. There are four individually-addressable independent disc-shaped WEs 10, located about 90° away from each other and placed between the ring and the disc areas of the CRE 12. WEs 10 are not electrically connected to each other. Each WE 10 disc is about 0.2-cm in diameter, has a surface area of about 0.03 cm$^2$. The minimum separation distance (d) between the each WE and the ring-disc CRE is about 0.1 cm. All the electrodes are set parallel to the holder 14. The holder and the supports are made from an inert material. The holder also houses the corrosion rate meter described below with reference to FIG. 2 and FIG. 4.

The Corrosion Rate Meter

FIG. 2 shows the ECRM, which adheres to principles of current-pulse chronovoltammtery. The ECRM sensor circuit 20 includes a current source generated by a power source 28 connected through different resistances $R_1$ 26 to $R_n$ 24. Selecting the resistance using the Relay 2 (not shown) determines the amplitude of the current. Relay 1 16 selects the duration of the current pulse. The current is applied between the WE 10 and CRE 12 of the ECRM through the galvanostat 22, and the polarization of the WE 10 is measured by the voltmeter/A-D converter 18. The voltmeter 18 has an input impedance greater than 10$^9$ ohms. A Galvanostat is an electronic instrument that controls the current through an electrochemical cell at a preset value. An external reader-head with a data link and power link 32 powers the system 20, reads and transfer the data via the data link 36 of the ECRM 20 to the computer 30.

Figure 3:
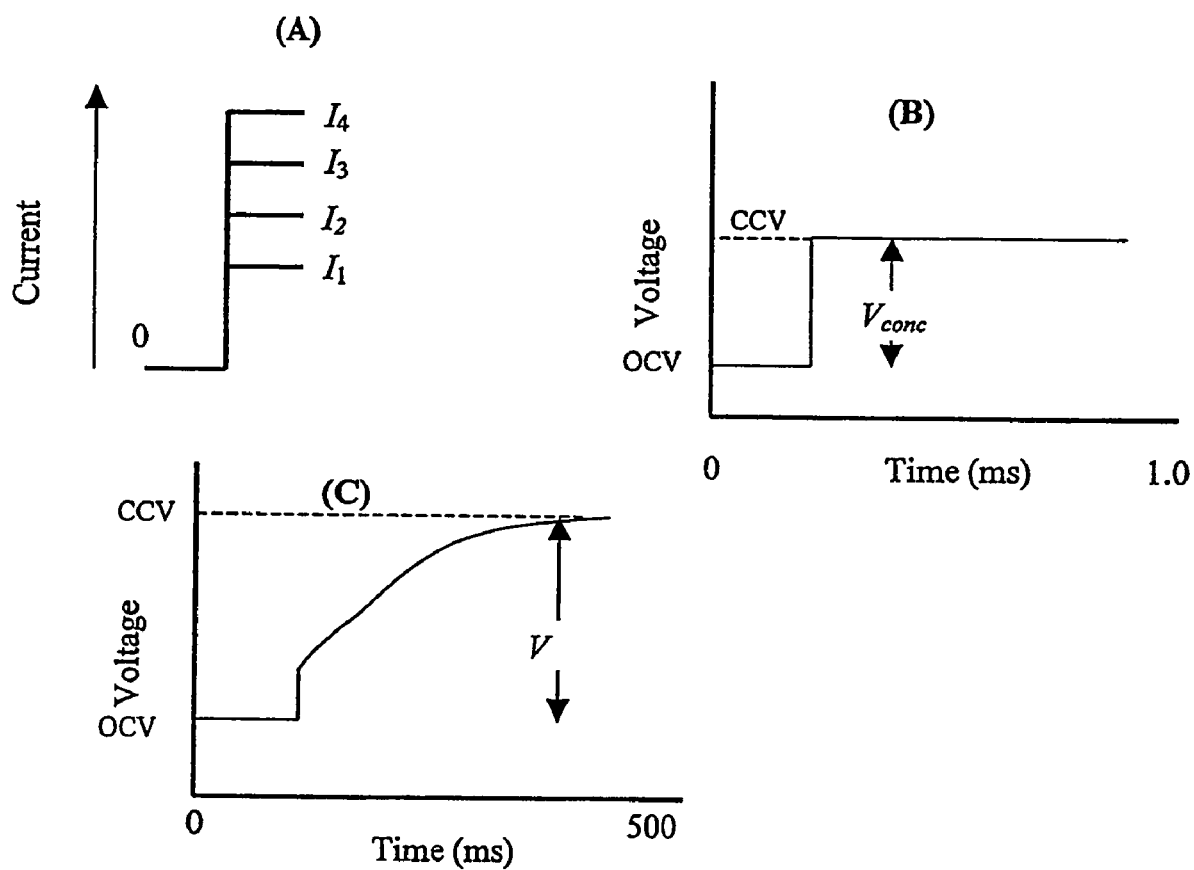
FIG. 3A is a graph of a series of current pulses, $I_1$ to $I_4$, applied one after another, for each I, the pulses are applied twice, first for a duration of 1 ms, and next over 500 ms, the current pulse sequence applied to measure $V_{conc}$ and V; and compute $V_p$.
FIG. 3B is a voltage/time response, 1 ms in duration, used to measure $V_{conc}$, the polarization is due to the electrolyte (concrete) resistance.
FIG. 3C is a voltage/time graph of the pulse, 500 ms in duration, used to measure V, $V_p$ is computed as $(V-V_{conc})$, and the plot of $V_p$/I provides, the polarization resistance, $R_p$, which is inversely proportional to the corrosion rate.

The ECRM technique may be viewed as an extension of the conductivity meter (CM) suggested in the patent application for the Smart Aggregate (SA). Both of them use a galvanostat 22 to inject a constant current between two electrodes WE 10 and CRE 12 over a fixed period, and measure the resulting difference in the voltage between them. In the CM, the two electrodes 10 and 12 have identical dimensions, and are made from material such as gold or platinum-coated gold. In the ECRM case, the WE 10 is made from the corroding metal, and has a different dimension from the CRE 12. However, there are several major differences between CM and ECRM 20. Unlike the CM, which uses a current pulse with fixed amplitude, the ECRM 20 employs current pulses with several different amplitudes. Furthermore, at each current amplitude, two pulses with two different durations are applied. The first pulse is about 1 ms long, and the second pulse is about 500 ms in duration. The voltage differences between the WE 10 and CRE 12 are measured before the pulse is applied, and the end of the pulse, e.g., at about 1 ms and about 500 ms. The schematic of the current pulses and typical current-time (I-t) responses at about 1 ms and about 500 ms are shown in FIG. 3.

The ECRM operation is performed by disconnecting the current source galvanostat 22 from WE 10 and CRE 12 and measuring the voltage difference between WE 10 and CRE 12. This is an open circuit voltage (OCV) between the two electrodes.

The measurement is performed as follows:
1. Set j=0, where j is an exemplary value from 0 to 4.
2. Increment j and set current pulse amplitude to $I_j$, the suggested amplitudes for the current pulses are in the ±0.1 to ±10 µA range;
3. Start the 1 ms current pulse at set amplitude and measure the voltage difference between WE 10 and CRE 12. This is the 1 ms closed circuit voltage ($CCV_{@1\ ms}$) between the two electrodes for the current pulse at set amplitude $I_j$;
4. Start the 500 ms current pulse with set amplitude and measure the voltage difference between WE 10 and CRE 12. This is the 500 ms closed circuit voltage ($CCV_{@500\ ms}$) between the two electrodes for the current pulse at set amplitude j. The difference between $CCV_{@1ms}$ and $CCV_{@500\ ms}$ provides $(V_p)_j$;
5. Repeat Steps 2–4 for current amplitude values of $I_2$ through $I_4$, as well as at $-I_1$, $-I_2$, $-I_3$, and $-I_4$ and estimate the value of $(V_p)_j$;

6. Make a graphical plot of I vs. $V_p$, with OCV as the origin. Estimate the slope of the plot of I vs. $V_p$. The slope provides the value of the polarization resistance, $R_p$, which is inversely proportional to the corrosion rate;
7. In a variation of this approach, j can be varied from ±1 to any other number.

The voltage difference for the 1-ms pulse represents the voltage drop across the electrolyte (concrete) resistance, and represented as $V_{conc}$. The voltage difference for the 500 ms pulse represents the voltage drop across the WE/electrolyte (concrete) interfacial resistance plus the voltage drop across the concrete resistance, and represented as $V_p$. $V_p=(V-V_{conc})$, and it represents the polarization at the WE/electrolyte (concrete) interface. The steps described above allow one to measure $V_p$ for a set of current pulses (I), typically in the range of ±0.1 to ±10 microamperes (μA). For the 0.071 cm² steel WE in concrete, and for I in the range of ±0.1 to ±10 μA, the anticipated range of $V_p$ is 0 to ±10 mV. The slope of the plot of I vs. $V_p$, provides polarization resistance $R_p$, which is inversely proportional to the corrosion rate, see D. C. Silverman, "Practical Corrosion Prediction Using Electrochemical Techniques" in *Uhlig's Corrosion Handbook*, Ed. R. W. Reive, Electrochemical Society Series, Second Edition, John Wiley & Sons, NY, 2000, p. 1179, and Peabody's Control of Pipeline Corrosion, Second Edition, Ed. R. L. Bianchetti. NACE International, TX, 2001, p. 307.

The electrical circuit for the ECRM is organized in such a way that it produces at least two, more usefully four different current pulses in each direction, current flowing from WE to CRE, and vice versa. The sequence for the current pulses can be generated using software or an analog circuit. Thus, the schematic in FIG. 3 can be rearranged in several ways to generate the current pulses. The voltage measurement circuit in the schematic has an input impedance that is greater $10^9$ ohms. Similar to the CM in SA, the ECRM can be powered by an external power source through inductive coupling. The data from the ECRM can be transmitted through RF to an external receiver. Thus, the ECRM can be immersed or buried in a medium, and it can remain passive, until it is activated by an external stimulus.

Application

The ECRM has a large number of applications, especially to measure corrosion rates in buried structures, for example, a metal, e.g., iron, steels, e.g., carbon steel, stainless steel, super alloy steels, etc., copper, zinc, aluminum, titanium, and alloys and combinations thereof, in concrete and pipelines in soil, or immersed structures such as metal tanks filled with and immersed in chemicals such as, for example, acids, bases or an alkali medium, e.g., potassium hydroxide, sodium hydroxide and mixtures thereof. Most specifically, it can be kept in the upstream of incoming corrosive agents well ahead of where the agents have a chance to reach the structure that can be damaged by corrosion. Any change, i.e., increase, in the corrosion rate of the sensor will indicate impending corrosion damage to the structure on the downstream side. By locating one or more sensors above the rebars, the corrosive effect of incoming corrosive agents, such as chloride or change in pH caused by $CO_2$ or acid rain, can be inferred before the corrosive chemical flux reaches the rebar. Thus, the ECRM corrosion sensor measures the impact of those changes, and provides an advanced warning before the rebars ever experience corrosion.

The ECRM is different from the chloride, conductivity, temperature, or pH sensors: the ECRM provides direct information on the impending corrosion to the structure. The rest of the sensors, provide indirect information on the impending corrosion to the structure. Thus, if the objective is to obtain a direct estimation of corrosion, then the ECRM is better than the rest of the sensors.

Pulse-Modulated Perturbation Signals

In an alternative embodiment of the present invention, the miniature instrumentation is developed for the purpose of generating a train of pulses and applying them to the ECRM sensor. Typical shapes of the applied Current-Time (I-t) pulse and the Voltage-Time (V-t) response are also described herein. Experimental results, estimates of corrosion rates obtained using a corrosion sensor embedded in concrete, and validation of the performance of the newly developed miniature instrument by an independent, commercial, bench-top instrument are described below. Those results show that the ECRM sensor, which includes the miniaturized chronovoltammetry/AC impedance instrumentation, performs well in concrete.

This embodiment describes pulse-modulated signal source that synthesizes an I-t signal equivalent of a sum of several sine wave-signals, which is quite unlike the above-described embodiment that synthesized and applied several square-shaped current pulses, but one pulse at a time.

The I-t perturbation signal (drive) is a sum of several sine wave signals at different frequencies, typically in the range of 0.05 to 1000 Hz. The resulting drive amplitude at each frequency is less than 1 microampere; the sine wave at any particular frequency is slightly phase-shifted from the others, such that the amplitude due to the sum of all the frequencies does not exceed 2 microampere current at any time. The I-t drive is applied to the electrode galvanodynamically, the required instrumentation for the galvanostat is also a part of the ECRM sensor. Applying a 2 microampere current on the 0.071 cm² area electrode in the sensor is equivalent to applying about 28 microampere current on a 1 cm² area electrode. If the area of the test electrode is designed to be different from 0.071 cm², then the amplitude of the I-t signal should be changed proportionately. The area change in the test electrode WE 10 may warrant an area change in the counter electrode CRE 12. The total duration of the I-t perturbation signal lasts for about 40 to about 80 seconds, so that the signal at every frequency completes several cycles during the course of the test, which helps to improve the signal/noise ratio in the V-t response. The typical V-t response is in the 0.1- to 100-mV range. Furthermore, one could apply the I-t perturbation signals of amplitudes that are different from the suggested 28 microampere/cm², but with caution. Applying a current of amplitude less than 56 microampere/cm² may not alter the outcome (estimated corrosion rate). Currents with amplitudes above 56 microampere/cm² may adversely affect the corrosion rate estimates. Currents below 14 microampere/cm² will cause the response signal (V-t) to be too small, affecting the accuracy of voltage measurement.

The I-t perturbation drive and the V-t response are analyzed using computer software, which employs a conventional mathematical technique known as Fourier analysis. The technique separates the individual frequency components from the mixture, and estimates the time-delay between the applied signal and the response at each frequency. The vector ratio for each voltage/current sine-wave pulse from the known time-sequence of the applied I-t pulse, and the V-t response is then estimated. The vector ratio is generally referred to as impedance, from which the rate of corrosion can be derived. The impedance is related to the corrosion rate through a quantity known as polarization resistance, $R_p$.

Note that the procedure described in the previous embodiment shown in FIG. 3 obtains $R_p$ from a plot of I vs. V. The approach of the present embodiment obtains $R_p$ from the so-called impedance plot. In both embodiments, $R_p$ provides an estimate of the corrosion rate.

ECRM Instrumentation

Figure 4:
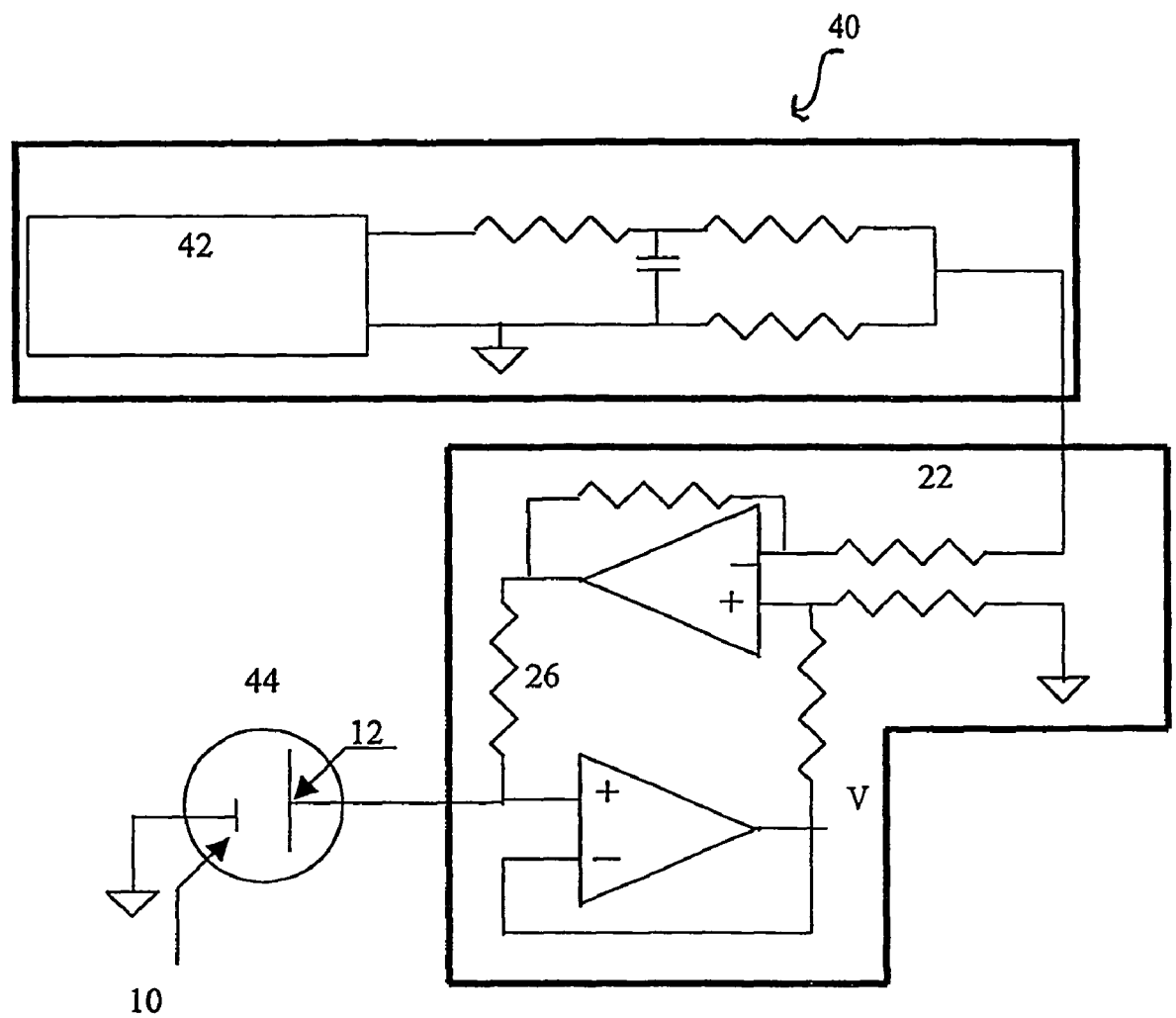
FIG. 4 is an electrical diagram representing the ECRM sensor circuit of the second embodiment, comprising a programmable electronic chip, a galvanostat, and an electrochemical cell of the present invention.

FIG. 4 shows the electrical diagram of the ECRM sensor 40. The sensor includes a miniaturized instrumentation for generating the I-t drive current using a programmable electronic Chip 42 such as, for example, MicroStamp11™, and a galvanostat 22, that is applied to the test metal embedded or immersed in the Electrochemical Cell 44. Microstamp11 is one of the world's smallest 68HC11 module manufactured by Technological Arts (819-B Yonge St., Toronto, Ontario, Canada M4W 2G9). The I-t pulse output of the Galvanostat 22 is shown in FIG. 5.

The Cell 44 contains the test metal WE 10, whose corrosion rate is being measured, and a non-corroding counter/reference electrode (CRE) 12, either embedded or immersed in the corrosive medium. The purpose of the Galvanostat 22 is to generate a current pulse (I), which perturbs the WE 10 in the Cell 44 and generates a voltage (V) response. The shape of the I-t signal is programmed into the Chip 42, which drives the Galvanostat 22.

A prototype of the ECRM was tested in the laboratory, in which the test metal, WE 10 was steel, cut in the form of a disc of small area 0.071 $cm^2$, and the CRE 12 was a large area of 10 $cm^2$ stainless steel in the form a of a cylinder, placed concentric to the WE 10. The WE 10 and the CRE 12 were embedded in concrete, and together they formed the Cell. The Chip 42 was programmed to output ten different sine wave voltage signals ($V_{chip}$), simultaneously, in the 0.1 to 100 Hz frequency range. The $V_{chip}$ was the input for the Galvanostat 22, which outputted a current signal I of amplitude equal to ($V_{chip}/R_1$). The $V_{chip}$ and the $R_1$ values are so selected to keep I at about 1 microampere. The Chip was programmed so that $V_{chip}$, and therefore I, would last for 50 seconds as the input to the Electrochemical Cell 44. During the 50-second-period, the lowest frequency component set at 0.1 Hz repeated itself five times, and the highest frequency component set at 100 Hz repeated itself 5,000 times. The flow of I through the Cell 44 generated a voltage, V across the Cell 44. Due to the large difference in the area between the CRE 12 and WE 10 (see FIG. 1), most of V was assumed to have occurred across the interface between WE 10 and concrete, with the rest across the resistance of the concrete, and little across the CRE 12-concrete interface.

The shape of a typical I and V is shown in FIGS. 5 and 6. The current pulse output from the Galvanostat shown in FIG. 5, is the input signal to the electrochemical cell 44 (FIG. 4). In the illustrated example, the current signal started at 8.5 second and ended at 58.5 second, for a total period of 50 seconds. The start time of the current signal can be set to any value, but the start time should be accurately recorded for the purpose of analysis.

FIG. 6 shows the V-t response by the electrochemical Cell 44, to the applied I-t perturbation. The I-t pulse is the resultant of the sum of several sine wave signals, each at a different frequency, and the signal at each frequency lasts for the entire duration of the sum. The instrument 42 (FIG. 4) performs the simple process of generating the 'summed up' signal. Note that the summed up signal can be deconvoluted, and its individual component separated either by using other instruments such as a Fast Fourier Transform (FFT) analyzer, or through mathematical techniques such as Fourier, Hadamand or Z transformation, all fairly well known techniques. The discussion above is based on the mathematical technique of Fourier transformation. The transformation allows estimation of the impedance, the vector ratio of I and V, at each frequency.

An onboard FFT analyzer may be built within the ECRM sensor 40. Instead of collecting a large time-array of I data and V data, and then analyzing it externally, a miniature FFT analyzer can be incorporated on-board of the ECRM sensor 40. The FFT analyzer will take the I-t signal shown in FIG. 5 and the V-t response shown in FIG. 6 through two of its input channels, analyze them, and output the impedance data at each frequency. Such an approach has two advantages. First, it will eliminate the need for transmitting large amounts of I-t and V-t data out of ECRM for analysis purpose; typically, one set of I-t and V-t data may contain anywhere between 1,000 to 100,000 data points. If an FFT analyzer is on-board the ECRM sensor, then the number of points transmitted out of it is only about 40, assuming the total number of frequencies in the signal are twenty. Second, the presence of onboard FFT analyzer will eliminate the need for computer software to conduct the Fourier transformation, thus reducing the complexity associated with data analysis. As a part of the ECRM technology development, a miniature FFT analyzer is being incorporated inside the ECRM sensor 40. The test results from the ECRM sensor 40 that includes the FFT analyzer will become available in the near future.

FIGS. 7A and 7B show the impedance values obtained for two different electrochemical Cells 44. Note that the impedance representation in the figure belongs to a category known as complex plane plot; the property of the interface between the electrode and the concrete is such, that it has the capacity to shift the applied current pulse and the resulting voltage response in the time domain. Due to this shift, the vector ratio between the voltage and the current should be calculated using complex algebra, an area of mathematics known to most engineers. Note that the shift depends upon the frequency of the applied signal, and the property of the electrode/concrete interface. However, in most cases, the impedance plot will have a shape that is reminiscent of a partial circle (quarter circle to semicircle). The diameter of the circle is the polarization resistance, $R_p$, which is related to the corrosion rate. The inset in FIG. 7a shows the electrical components in Module 12861. Note that the two instruments have measured and identified 6,800 ohms as the difference in the $Z_{real}$ values between 0.1 Hz and 100 Hz. Similarly, the $Z_{real}$ value at 100 Hz is 2,800 ohm, which is the sum of 1,000 ohm and 1,800 ohm. In a real corrosion cell, the $Z_{real}$ value at the high-frequency limit (100 Hz) would represent the electrolyte resistance (or the concrete resistance $R_{conc}$), and the difference in the $Z_{real}$ values between the low- and high-frequency limits (0.1 Hz and 100 Hz) would represent the $R_p$.

ECRM Data Analysis and System Validation

FIGS. 7A and 7B illustrate two sets of data collected on two types of electrochemical cells 44 (FIG. 4). One set was obtained on a "dummy" electrochemical cell with resistors and capacitors (Solatron Dummy Cell, ECI Test Module 12861) mimicking a metal/electrolyte (or steel/concrete) interface, and on a real Cell with steel embedded in concrete.

Within each set of data, there are two subsets, one collected using the miniature instrument 40 (FIG. 4), and another a bench-top, commercial impedance-measuring instrument (Solatron SI 1287/1250). The commercial instrument is used by the corrosion industry and was used herein as a standard to verify the newly designed miniature ECRM sensor 40 (FIG. 4).

The objective of experimenting with a dummy electrochemical cell is to provide an initial comparison between the two approaches without introducing the uncertainties that is sometimes present in a real corrosion cell. In its simplest form, the current-voltage behavior of the interface between the electrode and the concrete is similar to that of a capacitor connected in parallel to one resistor, and in series with a second resistor (see inset in FIG. 7B). The resistor in parallel with the capacitor is the polarization resistance ($R_p$), which is related to the corrosion rate. The second resistor, $R_{conc}$ is equivalent to the electrical resistance of the concrete. The capacitor, $C_{dl}$ indicates the state of the capacitance at the interface, therefore, the amount of corrosive chemicals (for example, chloride ions) adsorbed on the electrode surface. The main objective of the ECRM is to estimate $R_p$, thus the corrosion rate, although the response by the sensor to the applied signal will be affected by $R_{conc}$ and $C_{dl}$. In practice, no a priori information will be available on $R_p$, $R_{conc}$ or $C_{dl}$. Therefore, estimating those values using any instrument is questionable, unless the instrument is first calibrated with an electrical circuit with known circuit elements. The dummy electrochemical cell, with known elements of $R_p$, $R_{conc}$ and $C_{dl}$, served the purpose of calibrating the commercial bench-top unit, which in turn was used to validate the ECRM sensor. Without independent validation such as these, the usefulness of a newly developed corrosion rate meter cannot be established.

The two subsets of impedance data in FIG. 7a is the impedance due to the Solartron Dummy Cell, ECI Test Module 12861, obtained using Solartron SI 1287/1250 impedance measuring instrument, and the newly designed miniature instrument in FIG. 4. The circuit diagram of the Module 12861 is shown in the inset in FIG. 7a. In FIG. 7a, the two impedance plots have shapes that are fairy close to a semicircle, although there is more scatter in the data for the miniature instrument; the error in $R_p$ caused by the scatter is less than 10%, which is within acceptable experimental limits. The dummy cell had an equivalent of 6,800 ohms for the $R_p$. The diameter of the two semicircles matched the 6,800 ohm, suggesting that the commercial unit and the ECRM sensor do function properly.

The two subsets of data in FIG. 7B were obtained on a real electrochemical cell, also using the Solartron SI 1287/1250 and the ECRM sensor. The match between the two subsets is reasonable within the frequency range (0.1 Hz to 100 Hz) of the experiment. At the higher limit of the frequency (100 Hz), the imaginary component of the impedance is close to zero, and the real component of the impedance provides an estimate of the concrete resistance, $R_{conc}$. For steel in chloride-contaminated concrete, at all frequencies above 100 Hz, the real and imaginary components of the impedance converge at $R_{conc}$. At frequencies below 0.1 Hz (data not shown), the impedance is limited by mass transfer of the reactant (in this case, oxygen, which is the oxidizer). In this region, the $Z_{real}$ vs. $Z_{imaginary}$ plot tend to have a linear shape, with little information on $R_p$, hence it is not shown in the figure. Also shown in the figure is a simulated impedance data with an $R_p$=36,000 ohm, $C_{dl}$=0.119 mF, and $R_{conc}$=2,400 ohm; these values were first estimated by fitting the experimental impedance data to a (suppressed) semicircle. The close match between the simulated and the experimental data suggests that the electrode/concrete interface has a polarization resistance, $R_p$ of 36,000 ohms. The corresponding corrosion rate is seven mils/year.

Furthermore, the extremely large value of the capacitance (0.119 mF/0.078 $cm^2$ or 1.526 $mF/cm^2$) is indicative of chloride adsorbed on the steel surface. Thus, $C_{dl}$ value can be used to infer the presence of chloride, a potential corrosive agent, on steel buried in concrete. Measurement of $R_p$ provides the rate of corrosion, independent of the reagents (chloride, acid rain, mercury in rain or fresh water, carbon dioxide, microbes and so on) that cause the corrosion.

Several books on corrosion, including D. C. Silverman, "Practical Corrosion Prediction Using Electrochemical Techniques" in *Uhlig's Corrosion Handbook*, Ed. R. W. Reive, Electrochemical Society Series, Second Edition, John Wiley & Sons, NY, 2000, p. 1179, and Peabody's Control of Pipeline Corrosion, Second Edition, Ed. R. L. Bianchetti. NACE International, TX, 2001, p. 307, describe the procedure to convert $R_p$ to corrosion rate in units of mils/year. Typically, the conversion is made in three steps. First $R_p$ is converted to corrosion current, $I_{cor}$ using the formula $$I_{cor}=(1/2.303R_p)(b_c b_a/(b_c+b_a)),$$

where $b_c$ and $b_a$ are the cathodic and anodic Tafel slopes, which for steel in concrete are assumed to be 120 mV for $b_c$ and 60 mV for $b_a$. Next, $I_{cor}$ is converted to weight loss, w in $grams/cm^2/s$ as $$(w/at)=(I_{cor}tMW)/nF,$$

where MW is the molecular weight of iron (55.84), a is the area of the electrode in square centimeter, t is the time, n is the number of equivalence (2, for iron), and F is the Faraday constant (96,480 C). Taking into account the density, $\rho$ of the metal, (7.86 $g/cm^3$ for iron), the corrosion rate is expressed in conventional terms as $$\text{Corrosion rate}=(w/\rho at)\times 1.242\times 10^{10}\text{ mils/year}$$

The foregoing is considered as illustrative of the principles of the invention. Accordingly all suitable modifications and equivalents may be resorted to, falling within the scope of the invention considered in light of the appended claims.

What is claimed is:

1. An embeddable system for detecting and measuring corrosion in a structure susceptible to corrosion, said system including a plurality of embeddable corrosion rate meters (ECRM) for collecting corrosion measurements data and at least one computing device for analyzing said corrosion measurements, said system comprising:

at least one working electrode evenly separated from a counter electrode, wherein a separation distance between said at least one working electrode and said counter electrode determines an electrolyte medium resistance, said electrolyte medium resistance is less than or equal to a polarization resistance;

a signal generator for generating a current source, said current source is connected to a plurality of resistances for creating a plurality of current amplitudes;

a first selector for applying current through each of said plurality of resistances to said at least one working electrode and said counter electrode, wherein said current is applied via a galvanostat;

an external reader-head with a data link and power link connected to said computing device for powering said ECRM and transferring corrosion measurements data via said data link; and a programmable electronic chip having a voltage output, wherein said chip is programmed to include a voltage-time signal, said voltage-time signal including a plurality of sine waves; and said galvanostat for receiving and converting said voltage output into a current-time perturbation signal.

2. The system of claim 1, wherein said ECRM is between 1 and 5 centimeters in diameter and between 0.2 and 1 centimeters in height.

3. The system of claim 1, wherein said counter electrode is separated from said at least one working electrode by holder material.

4. The system of claim 1, wherein said working electrode is made from the same material as the structure being detected for corrosion.

5. The system of claim 4, wherein the material is a metal selected from the group consisting of iron, carbon steel, stainless steel, super alloy steel, copper, zinc, aluminum, titanium, and alloys and combinations thereof.

6. The system of claim 1 wherein the structure is a rebar, storage tank, chamber, duct, tube or composite material.

7. The system of claim 1, wherein said counter electrode is made from a non-corroding inert material.

8. The system of claim 7, wherein the non-corroding inert material is selected from the group consisting of titanium oxide and ruthenium oxide, graphite, dimensionally stable palladium-coated titanium, and steel.

9. The system of claim 1, further comprising:
a second selector for selecting the duration of a current pulse; and,
a voltmeter and A-D converter for measuring polarization of said working electrode, wherein said voltmeter has an input impedance greater than $10^9$ ohms.

10. The system of claim 1, wherein said corrosion measurements data is used for graphing a plot of $I_j$ vs. $(V_p)_j$, with open circuit voltage OCV as the origin and estimating a slope of the plot of $I_j$ vs. $(V_p)_j$, wherein said slope provides the value of the polarization resistance, $R_p$, which is inversely proportional to the corrosion rate.

11. The system of claim 1, wherein said corrosion measurements data is obtained by disconnecting said galvanostat from said working electrode and said counter electrode and measuring a voltage difference between said working electrode and said counter electrode.

12. The system of claim 1, further comprising a unique electronic radio-frequency ID for identification of said ECRM.

13. In a system including:
an embeddable system for detecting and measuring corrosion in a structure susceptible to corrosion, said system including a plurality of embeddable corrosion rate meters (ECRM) for collecting corrosion measurements data and at least one computing device for analyzing said corrosion measurements, said system comprising:

at least one working electrode evenly separated from a counter electrode, wherein a separation distance between said at least one working electrode and said counter electrode determines an electrolyte medium resistance, said electrolyte medium resistance is less than or equal to a polarization resistance;

a signal generator for generating a current source, said current source is connected to a plurality of resistances for creating a plurality of current amplitudes;

a first selector for applying current through each of said plurality of resistances to said at least one working electrode and said counter electrode, wherein said current is applied via a galvanostat; and an external reader-head with a data link and power link connected to said computing device for powering said ECRM and transferring corrosion measurements data via said data link, a method of obtaining the corrosion measurements data, comprising the steps of:

a) disconnecting said galvanostat from said working electrode and said counter electrode; and b) measuring a voltage difference between said working electrode and said counter electrode, wherein step b) comprises:

setting a variable j to 0, where j is an integer value from 0 to n;

i) incrementing j and setting a current pulse amplitude to $I_j$, wherein amplitudes for current pulses are in the ±0.1 to ±10 μA range;

ii) starting a 1 ms current pulse at pre-set amplitude and measuring said voltage difference between working electrode and said counter electrode, storing said difference as 1 ms closed circuit voltage ($CCV_{@1\ ms}$) between said working electrode and said counter electrode for the 1 ms current pulse at set amplitude $I_j$;

iii) starting a 500 ms current pulse at pre-set amplitude and measuring said voltage difference between working electrode and said counter electrode, storing said difference 500 ms closed circuit voltage ($CCV_{@500\ ms}$) between said working electrode and said counter electrode for the 500 ms current pulse at set amplitude $I_j$, wherein a difference between $CCV_{@1\ ms}$ and $CCV_{@500\ ms}$ provides $(V_p)_j$;

repeating steps i)–iii, for current amplitude values of $I_2$ through $[I_j]I_n$, as well as at $-I_1$, through $[-I_j]-I_n$, and estimating the value of $(V_p)_j$ for each $I_j$ value.

* * * * *